US011234687B2

(12) United States Patent
Deuel et al.

(10) Patent No.: US 11,234,687 B2
(45) Date of Patent: Feb. 1, 2022

(54) TISSUE ENGAGEMENT DEVICE

(71) Applicant: BOSTON SCIENTIFIC SCIMED, INC., Maple Grove, MN (US)

(72) Inventors: Christopher R. Deuel, Melrose, MA (US); Danny Shu-Huan Lee, Cambridge, MA (US); Paul Smith, Smithfield, RI (US); Routha Sim, Lowell, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 200 days.

(21) Appl. No.: 16/399,963

(22) Filed: Apr. 30, 2019

(65) Prior Publication Data

US 2019/0357907 A1 Nov. 28, 2019

Related U.S. Application Data

(60) Provisional application No. 62/674,774, filed on May 22, 2018.

(51) Int. Cl.
*A61B 17/02* (2006.01)
*A61B 17/08* (2006.01)
*A61B 17/00* (2006.01)

(52) U.S. Cl.
CPC ........ *A61B 17/0218* (2013.01); *A61B 17/083* (2013.01); *A61B 2017/00367* (2013.01); *A61B 2017/081* (2013.01)

(58) Field of Classification Search
CPC ...... A61B 2017/00367; A61B 17/0218; A61B 17/1285; A61B 17/083; A61B 2017/081;
(Continued)

(56) References Cited

U.S. PATENT DOCUMENTS

| 3,958,576 A | 5/1976 | Komiya |
| 5,242,456 A | 9/1993 | Nash et al. |

(Continued)

FOREIGN PATENT DOCUMENTS

| DE | 19801897 A1 | 7/1999 |
| WO | 2016111755 A1 | 7/2016 |

(Continued)

OTHER PUBLICATIONS

Sakamoto, N., et al., "Endoscopic submucosal dissection of large colorectal tumors by using a novel spring-action S-O clip for traction (with video)", Gastrointestinal Endoscopy 69(7):1370-1374 (2009).

(Continued)

*Primary Examiner* — Melanie R Tyson
*Assistant Examiner* — Paige A Codrington
(74) *Attorney, Agent, or Firm* — Kacvinsky Daisak Bluni PLLC

(57) ABSTRACT

Medical devices and methods of using medical devices are disclosed. An example tissue engagement device includes a first actuation member including a body coupled to a first jaw and a second jaw at a pivot point, wherein the body is designed to shift between a first configuration and a first compressed configuration and a second actuation member coupled to the first actuation member at the pivot point and at a fixation point, wherein the second actuation member is designed to shift between a second configuration and a second compressed configuration. Further, shifting the first actuation member from the first configuration to the first compressed configuration, shifting the second actuation member from the second configuration to the second compressed configuration, or both, shifts the first jaw and the second jaw between a closed configuration and an open configuration.

18 Claims, 11 Drawing Sheets

(58) Field of Classification Search
CPC . A61B 17/122; A61B 17/08; A61B 17/12009; A61B 17/68; A61B 17/84; A61B 2017/12004
USPC .......................................................... 606/151
See application file for complete search history.

(56) References Cited

U.S. PATENT DOCUMENTS

| | | | |
|---|---|---|---|
| 5,904,702 A * | 5/1999 | Ek | A61B 17/29 606/206 |
| 8,038,612 B2 | 10/2011 | Paz | |
| 8,172,870 B2 | 5/2012 | Shipp | |
| 8,397,335 B2 | 3/2013 | Gordin et al. | |
| 8,945,155 B2 | 2/2015 | Gordin et al. | |
| 9,463,003 B2 | 10/2016 | Gordin et al. | |
| 10,111,699 B2 * | 10/2018 | Boudreaux | A61B 18/1442 |
| 10,143,459 B2 | 12/2018 | Heftman | |
| 2002/0065534 A1 * | 5/2002 | Hermann | A61B 17/0643 606/205 |
| 2003/0149446 A1 * | 8/2003 | Shuman | A61B 17/12 606/205 |
| 2005/0021062 A1 * | 1/2005 | Dennis | A61B 17/1227 606/157 |
| 2005/0256533 A1 * | 11/2005 | Roth | A61F 5/0083 606/167 |
| 2006/0047290 A1 * | 3/2006 | Otten | A61B 17/128 606/157 |
| 2008/0255427 A1 * | 10/2008 | Satake | A61B 17/083 600/204 |
| 2008/0319455 A1 * | 12/2008 | Harris | A61F 5/0089 606/139 |
| 2010/0004678 A1 * | 1/2010 | Garica | A61B 17/30 606/210 |
| 2010/0174150 A1 * | 7/2010 | Park | A61B 17/0218 600/218 |
| 2011/0130773 A1 * | 6/2011 | Saliman | A61B 17/0482 606/145 |
| 2013/0030462 A1 | 1/2013 | Keating et al. | |
| 2014/0142597 A1 * | 5/2014 | Winkler | A61B 17/122 606/157 |
| 2014/0378998 A1 * | 12/2014 | Rizzuto | A61B 34/30 606/130 |
| 2016/0317157 A1 | 11/2016 | Bacher | |
| 2017/0238935 A1 * | 8/2017 | Shi | A61B 17/1285 |
| 2018/0014876 A1 * | 1/2018 | Allen, IV | A61B 17/122 |
| 2018/0036008 A1 * | 2/2018 | Ramsey | A61B 17/122 |
| 2019/0336728 A1 * | 11/2019 | Unger | A61M 25/0026 |
| 2019/0343540 A1 * | 11/2019 | Morales | A61B 17/2833 |
| 2019/0357907 A1 * | 11/2019 | Deuel | A61B 17/2841 |
| 2020/0046366 A1 * | 2/2020 | Baril | A61B 17/1227 |
| 2020/0360023 A1 * | 11/2020 | Bagley | A61B 17/0218 |
| 2020/0367892 A1 * | 11/2020 | Sauter | A61B 17/1227 |
| 2020/0383685 A1 * | 12/2020 | Sauter | A61B 17/1227 |

FOREIGN PATENT DOCUMENTS

| | | |
|---|---|---|
| WO | 2018027113 A1 | 2/2018 |
| WO | 2018075879 A1 | 4/2018 |

OTHER PUBLICATIONS

Fujii, T., et al., "A novel endoscopic suturing technique using a specially designed so-called "8-ring" in combination with resolution clips (with videos)", Gastrointestinal Endoscopy 66(6):1215-1220 (2007).

Matsumoto, K., et al., "T1594: A New Traction Device for Gastric Endoscopic Submucosal Dissecton (ESD): Two-Point Fixed by Latex Traction for Early Gastric Cancer", Gastrointestinal Endoscopy, 71(5):AB317 (2010).

Imaeda, H., et al., "Advanced endoscopic submucosal dissection with traction", World Journal of Gastrointestinal Endoscopy 6(7):286-295 (2014).

Sakamoto, N., et al.,"'Loop Clip' a new closure device for large mucosal defects after EMR and ESD", Endoscopy 40: E97-E98 (2008).

Fujihara, S., et al., "Management of a large mucosal defect after duodenal endoscopic resection", World Journal of Gastroenterology, 22(29):6595-6609 (2016).

Miori, H., et al., "The Loop Clip is Useful for Closing Large Mucosal Defects After Colorectal Endoscopic Submucosal Dissection: A Preliminary Clinical Study", Digestive Endoscopy 23:330-331 (2011).

Tsuji, K., et al., "Recent traction methods for endoscopic submucosal dissection", World Journal of Gastroenterology, 22(26):5917-5926 (2016).

Ritsuno, H., et al., "Prospective clinical trial of traction device-assisted endoscopic submucosal dissection of large superficial colorectal tumors using the S-O clip", Surgical Endoscopy 28:3143-3149 (2014).

Sakamoto, N., et al., "The facilitation of a new traction device (S-O clip) assisting endoscopic submucosal dissection for superficial colorectal neoplasms", Endoscopy, 40:E94-E95 (2008).

Takeda, T., et al., "Traction device to remove an adenoma in the appendiceal orifice by endoscopic submucosal dissection". Endoscopy 45:E239-E240 (2013).

Kato, M., et al., "Technical feasibility of line-assisted complete closure technique for large mucosal defects after colorectal endoscopic submucosal dissection", Endoscopy International Open, 5(1):E11-E16 (2017) DOI: http://dx.doi.org/10.1055/S-0042-121002.

International Search Report and Written Opinion for International application No. PCT/US2019/030081, dated Aug. 14, 2019, 12 pages.

* cited by examiner

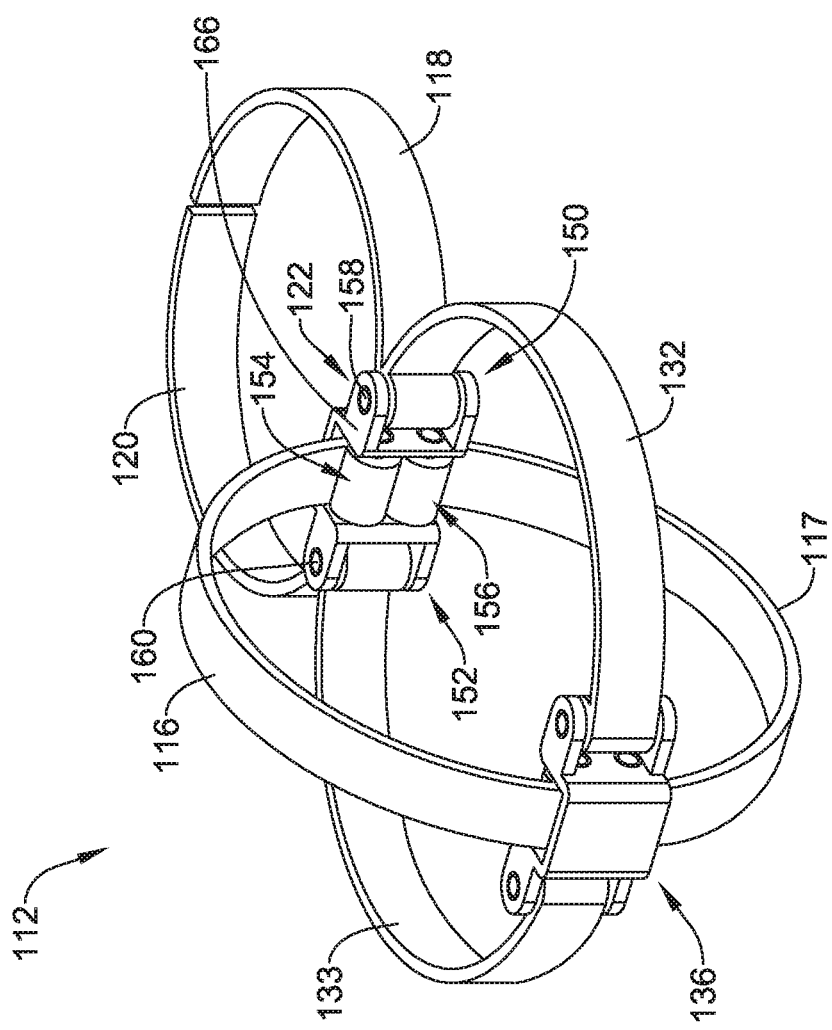

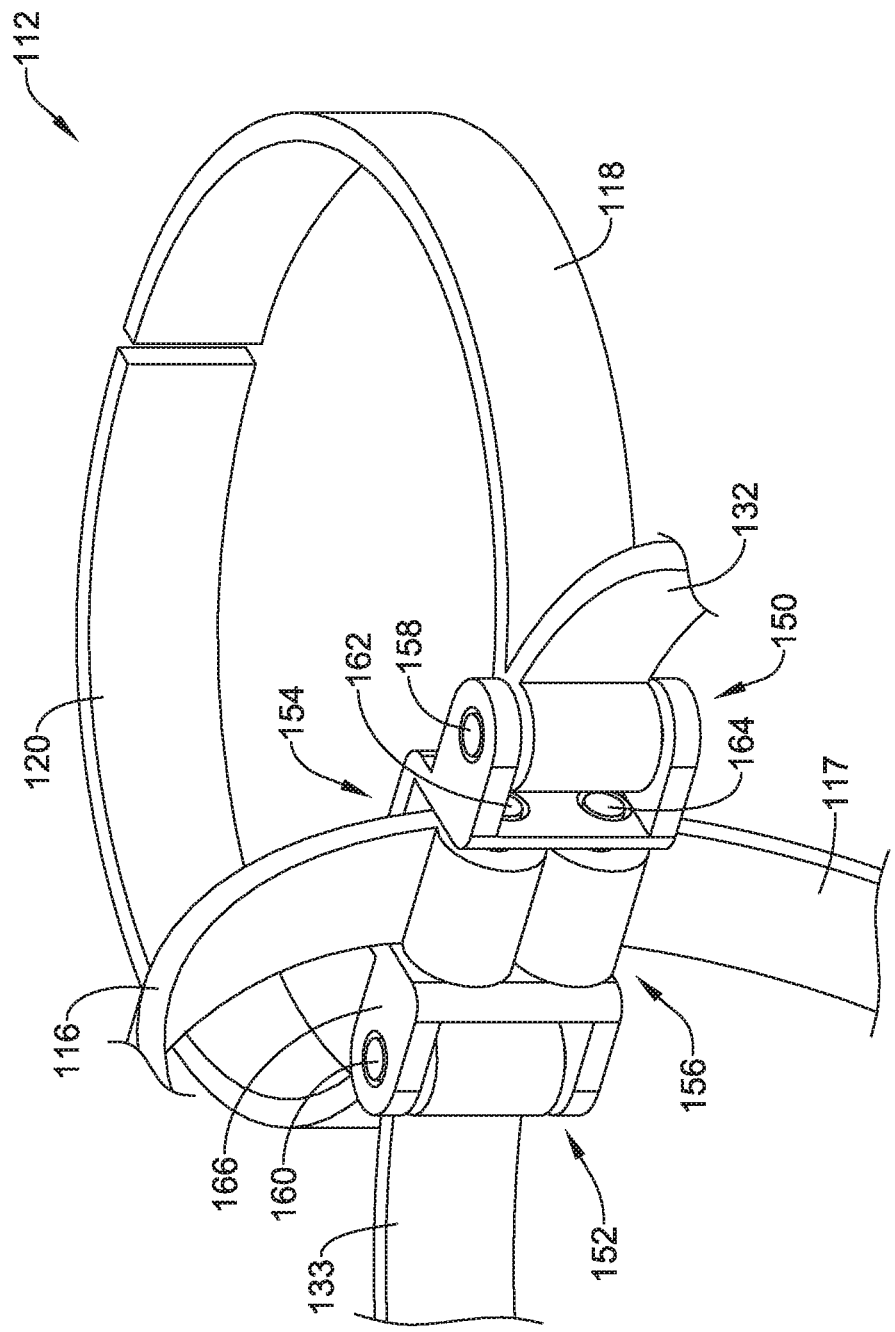

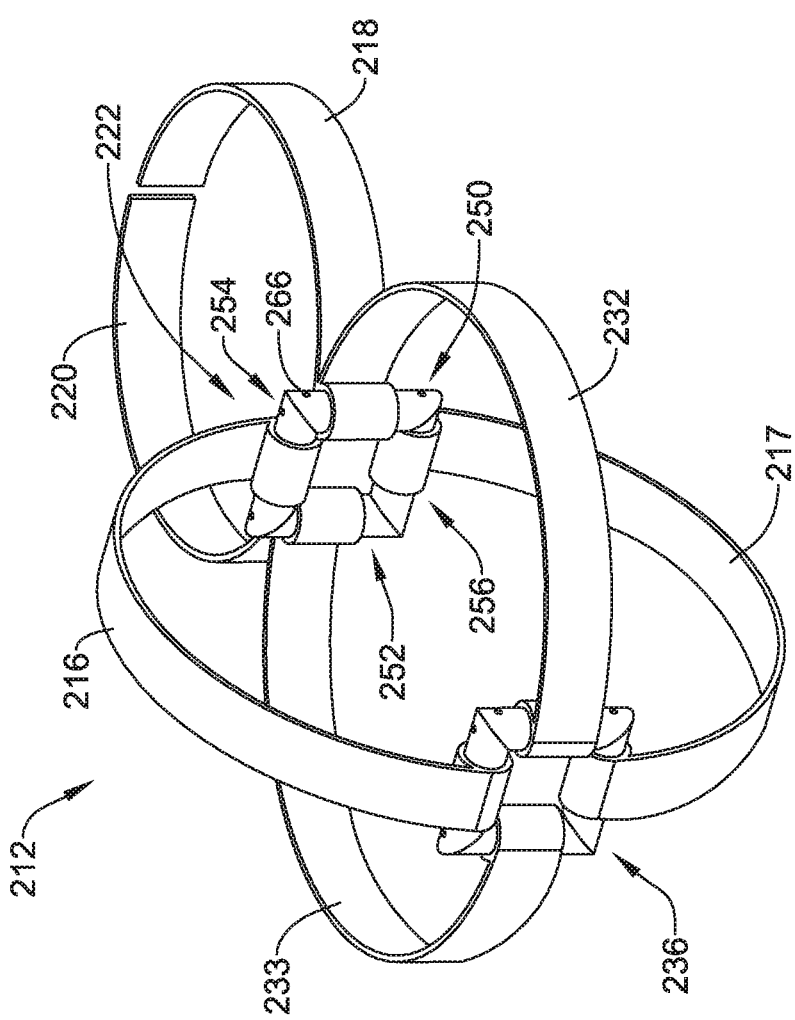

TISSUE ENGAGEMENT DEVICE

CROSS-REFERENCE TO RELATED APPLICATIONS

This application claims the benefit of priority under 35 U.S.C. § 119 of U.S. Provisional Application No. 62/674,774, filed May 22, 2018, the entire disclosure of which is hereby incorporated by reference.

TECHNICAL FIELD

The present disclosure pertains to medical devices, and methods for manufacturing medical devices. More particularly, the present disclosure relates to tissue manipulation devices.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages.

BRIEF SUMMARY

This disclosure provides design, material, manufacturing method, and use alternatives for medical devices. An example tissue engagement device includes a first actuation member including a body coupled to a first jaw and a second jaw at a pivot point, wherein the body is designed to shift between a first configuration and a first compressed configuration and a second actuation member coupled to the first actuation member at the pivot point and at a fixation point, wherein the second actuation member is designed to shift between a second configuration and a second compressed configuration. Further, shifting the first actuation member from the first configuration to the first compressed configuration, shifting the second actuation member from the second configuration to the second compressed configuration, or both, shifts the first jaw and the second jaw between a closed configuration and an open configuration.

Alternatively or additionally to any of the embodiments above, wherein the second actuation member is positioned substantially perpendicular to the first actuation member.

Alternatively or additionally to any of the embodiments above, wherein body, the first jaw and the second jaw are formed from a monolithic member.

Alternatively or additionally to any of the embodiments above, wherein the body, the second actuation member or both the body and the second actuation member include an arcuate portion.

Alternatively or additionally to any of the embodiments above, wherein the body, the second actuation member or both the body and the second actuation member are substantially circular.

Alternatively or additionally to any of the embodiments above, wherein the body, the second actuation member or both the body and the second actuation member are substantially ovular.

Alternatively or additionally to any of the embodiments above, wherein shifting the first actuation member, the second actuation member or both the first and second actuation members rotates the first jaw and the second jaw around the pivot point.

Alternatively or additionally to any of the embodiments above, further comprising a compression membrane positioned around at least a portion of the body, the second actuation member or both the body and the second actuation member.

Alternatively or additionally to any of the embodiments above, wherein the first jaw and the second jaw are biased in the closed configuration.

Another tissue engagement device includes:
a first actuation member including a first end having a first jaw, a second end having a second jaw, and a looped region positioned between the first jaw and the second jaw, wherein the first jaw, the second jaw and the looped region lie within a first plane; and
a second actuation member pinned to the first actuation member at a pivot point and a fixation point, wherein the second actuation member lies in a second plane offset from the first plane;
wherein actuation of the first actuation member, the second actuation member or both the first and second actuation members shifts the first jaw and the second jaw between a closed configuration and an open configuration.

Alternatively or additionally to any of the embodiments above, wherein the second plane is positioned substantially perpendicular to the first plane.

Alternatively or additionally to any of the embodiments above, wherein first actuation member, the first jaw and the second jaw are formed from a monolithic member.

Alternatively or additionally to any of the embodiments above, wherein the first actuation member, the second actuation member or both the first and the second actuation members include an arcuate portion.

Alternatively or additionally to any of the embodiments above, wherein the first actuation member, the second actuation member or both the first and the second actuation members are substantially circular.

Alternatively or additionally to any of the embodiments above, wherein the first actuation member, the second actuation member or both the first and the second actuation members are substantially ovular.

Alternatively or additionally to any of the embodiments above, wherein actuation of the first actuation member, the second actuation member or both the first and second actuation members rotates the first jaw and the second jaw around the pivot point.

Alternatively or additionally to any of the embodiments above, further comprising a compression membrane positioned around at least a portion of the first actuation member, the second actuation member or both the first and the second actuation member.

Alternatively or additionally to any of the embodiments above, wherein the first jaw and the second jaw are biased in the closed configuration.

Another tissue engagement member includes:
an actuation assembly coupled to a pair of jaws, wherein the pair of jaws extends away from the actuation assembly, and wherein the actuation assembly includes a first actuation member coupled to a second actuation member at a first connection point;
wherein the first actuation member lies within a first plane, and wherein the second actuation member lies with a second plane offset from the first plane;

wherein actuation of the actuation assembly shifts the pair of jaws between a first configuration and a second open configuration.

Alternatively or additionally to any of the embodiments above, wherein the first actuation member, the second actuation member or both the first and the second actuation members includes an arcuate portion.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which:

FIG. 9 is a perspective view of another tissue engagement device;

FIG. 10 is a perspective view of the tissue engagement device shown in FIG. 9;

FIG. 11 is a perspective view of another example tissue engagement device.

Figure 1:
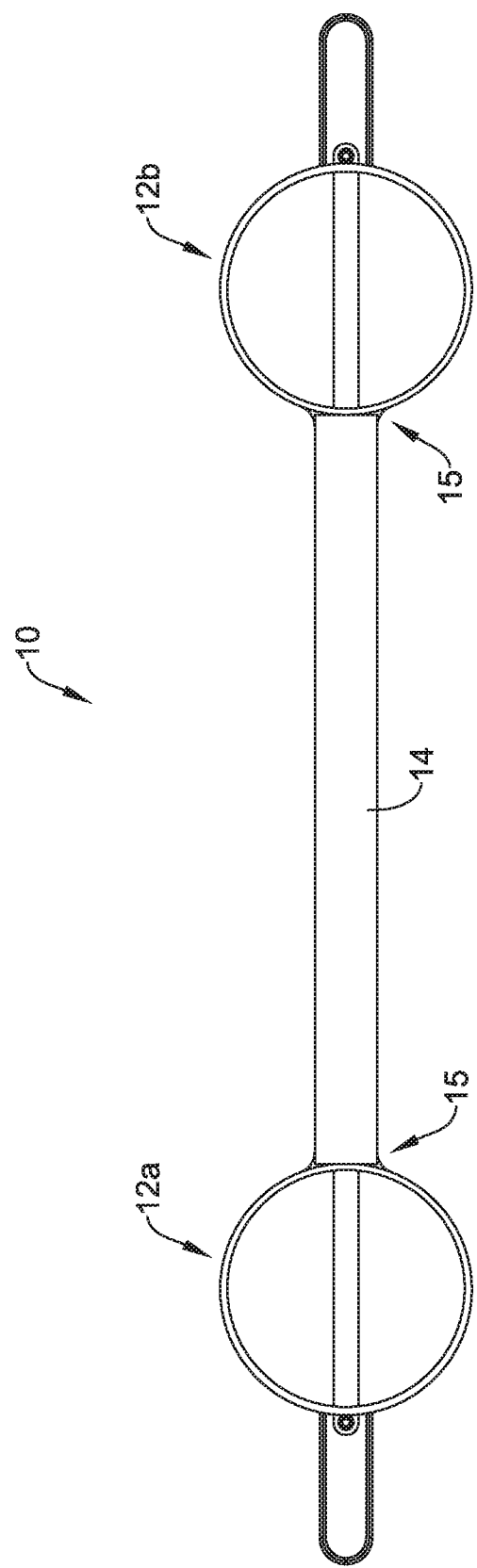
FIG. 1 is a perspective view of an example tissue retraction device.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used in connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

A number of medical procedures, including intravascular procedures, procedures along the digestive and/or biliary tract, thoracic procedures, etc. utilize medical devices to access tissue intended for removal (e.g., "target tissue") within the body. For example, in some current medical procedures (e.g., Endoscopic Submucosal Dissection (ESD), Peroral Endoscopic Myotomy (POEM), cholecystectomy, Video-Assisted Thoracoscopic Surgery (VATS)), physicians may utilize an endoscope or similar medical device to access and remove cancerous lesions. Further, as part of the procedure, the physician may utilize an endoscope capable of both accessing the target tissue site while also permitting a cutting device to be deployed therethrough to excise the target tissue. Additionally, in some instances, the endoscope may incorporate features which assist the physician in visualizing and performing the tissue dissection procedure. For example, some endoscopes may include a light and/or camera designed to illuminate the body lumen as the scope is navigated and positioned adjacent to the target tissue site. Additionally, some endoscopes may also include a lumen (e.g., a working channel) through which a cutting member or other accessory medical devices may be deployed and utilized.

While physicians are becoming more proficient at extracting cancerous lesions from within the body (e.g., within the digestive tract, abdominal cavity, thoracic cavity, etc.), the extraction methods continue to be inefficient and time-consuming. For example, in some instances poor visualization of the tissue dissection process may result in a prolonged tissue dissection procedure. In another example, the actual tissue that the physician is attempting to dissect may, itself, obstruct the pathway of the tools which the physician is using during the procedure. Therefore, in some instances it may be desirable to utilize a medical device which assists in improving the visualization of the target tissue while also mitigating the obstruction of dissection tools the physician is utilizing. Therefore, in some instances it may be desirable to utilize a tissue retraction device which lifts and retracts the region of tissue to be dissected by the physician. Disclosed herein are medical devices such as tissue retraction devices, tissue engagement devices and delivery systems that are designed to lift and retract the target tissue.

FIG. 1 is a plan view of an example tissue retraction device 10. The tissue retraction device 10 may include a first engagement member 12a coupled to a second engagement member 12b. Each of the engagement members 12a and 12b may be referred to as a clip, clasp, fastener, clamp, etc. For simplicity purposes, the following description will describe the engagement member 12a, however, it can be appreciated that the engagement member 12b may include all of the features and functionality described with respect to engagement member 12a.

Additionally, FIG. 1 illustrates that the first engagement member 12a may be coupled to the second engagement member 12b by a tether member 14. The tether member 14 may include a first end and a second end, wherein each of the first end and the second end is coupled to the engagement members 12a, 12b via a coupling member 15. The tether 14 may be referred to as a band, rope, cord, leash, strap, strand, etc. The tether 14 may include a variety of cross-sectional geometries. For example, the tether 14 may be circular, rectangular, triangular, or the like. Further, the tether 14 may be bioabsorbable. Further, the tether 14 may be constructed from an elastomeric material such as latex, Nitrile® rubber, ethylene propylene diene rubber, silicone rubber, chloroprene, polychloroprene (e.g., Neoprene), polyolefin, thermoplastic elastomer, polyisoprene, etc. The tether 14 may elongate from a first, unelongated (e.g., relaxed) position to a second, elongated position. It can be appreciated that when the tissue retraction device 10 is in an elongated position, the tissue retraction device 10 is in tension, and therefore, includes a retraction force which is pulling the first engagement member 12a toward the second engagement member 12b.

Figure 2:
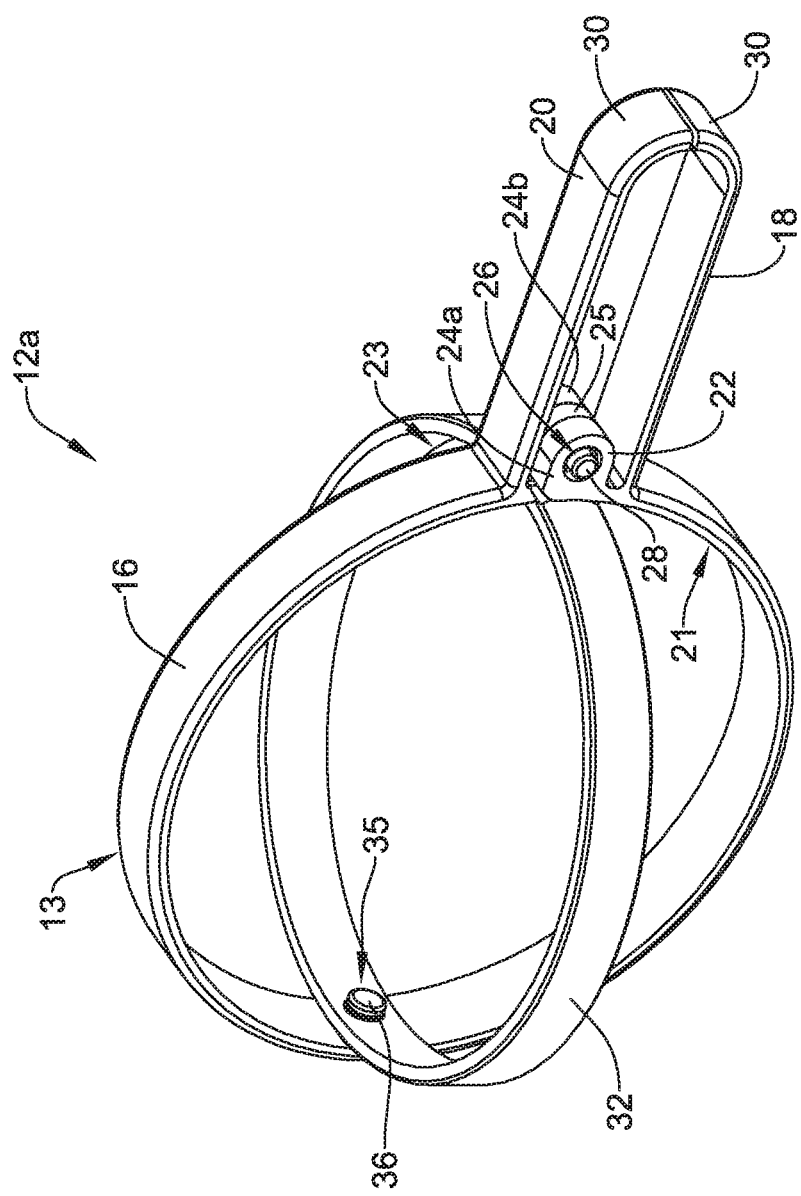
FIG. 2 is a perspective view of an example tissue engagement device.

FIG. 2 illustrates a perspective view of the first engagement member 12a. The engagement member 12a may include a body portion 16. The body portion 16 may be coupled to a first jaw 18 and a second jaw 20 at a pivot point 22. The combination of the body 16, the first jaw 18 and the second jaw 20 may be referred to as a first actuation member 13 herein. Each of the first jaw 18 and the second jaw 20 may include a curved region 30. The curved regions 30 may be utilized to grasp and/or engage tissue adjacent to a target tissue site. In some examples, the curved regions 30 may be described as a "tooth." Further, while FIG. 2 illustrates that the curved regions 30 may include a single, flat-faced tooth member, this is not intended to be limiting. Rather, the curved regions 30 may include one or more teeth. While not shown in FIG. 2, it is contemplated that the teeth may be spaced from one another and/or interdigitate with one another. A variety of different combinations and orientations of teeth are contemplated.

FIG. 2 illustrates that the body portion 16 may be positioned between the first jaw 18 and the second jaw 20. The body portion 16 may include an arcuate portion. In some instances, the body portion 16 may include a curve, loop, arc, etc. For example, the body portion 16 may be substantially circular-shaped. However, this is not intended to be limiting. Rather, it can be appreciated that the body 16 may include many different shapes. For example, the body 16 may be rectangular, ovular, square, hexagonal, polygonal, etc.

Additionally, as discussed above, the body portion 16 may include a first end region 21 from which the first jaw 18 extends away therefrom and a second end region 23 from which the second jaw 20 extends away therefrom. In some examples, the body 16, the first jaw 18 and the second jaw 20 may be formed as a monolithic structure. In other words, the body 16, the first jaw 18 and the second jaw 20 may be formed as a single, continuous piece of material. However, in other examples, the first jaw 18 and/or the second jaw 20 may be separate components from the body 16, whereby each of the first jaw 18 and the second jaw 20 may be separately attached to the first end region 21 and the second end region 23 of the body 16, respectively.

Figure 4:
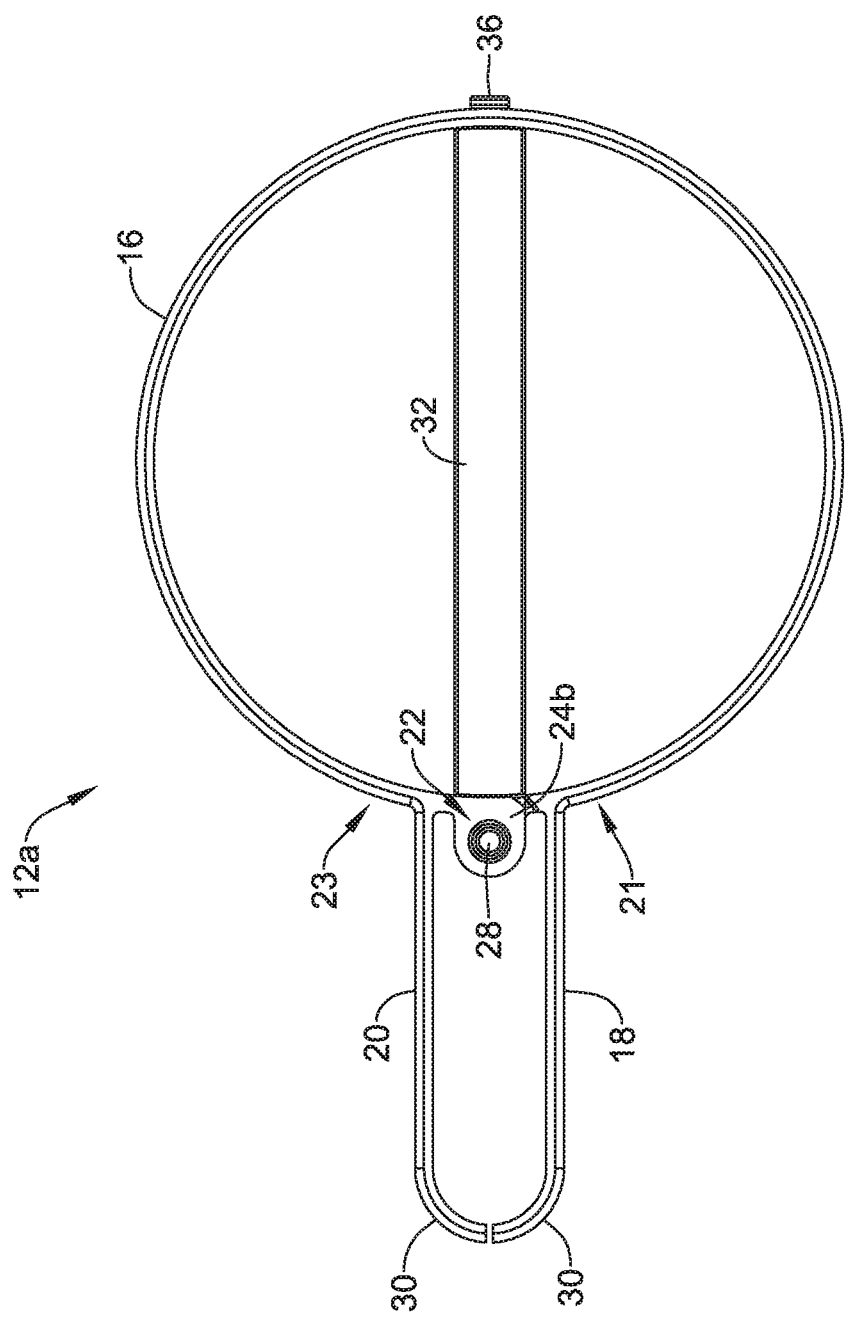
FIG. 4 is a side view of the tissue engagement device shown in FIG. 1.

FIG. 2 further illustrates that the first engagement member 12a may include a pivot point 22 which may include a first attachment portion 24a positioned adjacent to a second attachment portion 24b (the attachment portion 24b is more clearly shown in FIG. 4). In some examples, the geometry and/or shape of the first attachment portion 24a may mirror the geometry and/or shape of the second attachment portion 24b. Further, in some examples, the first attachment member 24a may extend away from the first end region 21 of the body while the second end region 23 may extend away from the second end region 23 of the body 16.

Figure 3:
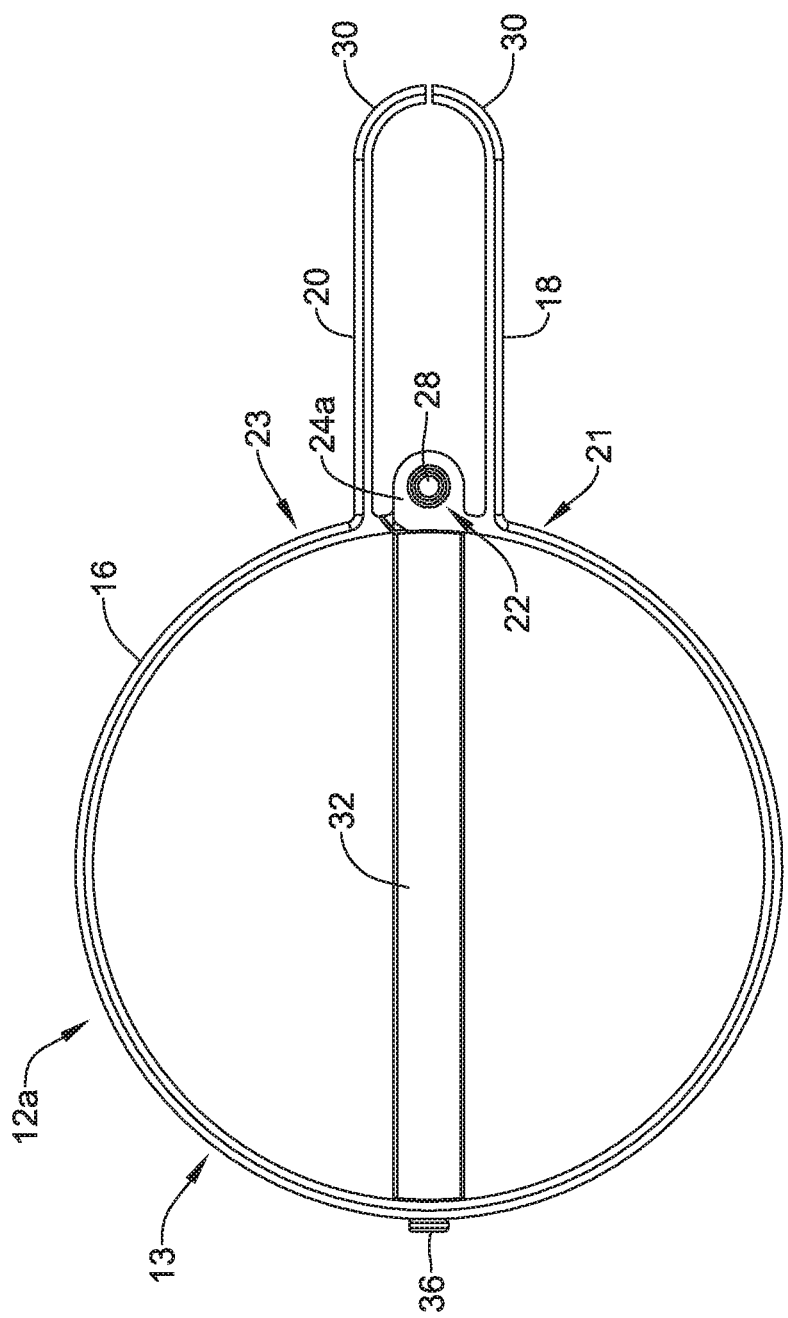
FIG. 3 is a side view of the tissue engagement device shown in FIG. 1.

Each of the first attachment member 24a may include a first aperture 26a while the second attachment member 24b may include a second aperture 26b (not shown in FIG. 2, but shown in FIG. 3). Each of the first aperture 26a and the second aperture 26b may extend through the wall thickness of each of the first attachment member 24a and the second attachment member 24b.

Additionally, FIG. 2 illustrates that the first engagement member 12a may include a second actuation member 32. In some examples, the second actuation member may be coupled to the body 16 of the first actuation member 13 at the pivot point 22. For example, FIG. 2 illustrates that the second actuation member 32 may include a projection 34 which includes a third aperture (not shown in FIG. 2, but more clearly shown in FIG. 5) which may be positioned adjacent to the first attachment portion 24a and the second attachment portion 24b. Further, FIG. 2 illustrates that the first attachment member 24a, the second attachment member 24b and the second actuation member 32 (via the projection 34) may be coupled to one another via a first pin 28. In other words, the first attachment member 24a, the second attachment member 24b and the second actuation member 32 may be aligned such that the pin 28 may extend through the first aperture 26a of the first attachment portion 24a, the second aperture 26b of the second attachment portion 24b and the third aperture of the second actuation member 32.

However, in other examples, the first attachment member 24a, the second attachment member 24b and the second actuation member 32 (via the projection 34) may be coupled to one another via other design configurations. Further, other design configurations may be utilized in place of the pin 28. For example, design configurations including living hinges, interfering elements, trapped linkages and/or a pivot ball may be utilized.

Additionally, FIG. 2 illustrates that the second actuation member 32 may be coupled to the body 16 of the first actuation member 13 at a connection point 35. For example, FIG. 2 illustrates that the second actuation member 32 may be coupled to the body 16 of the first actuation member 13 via a pin 36. However, while FIG. 2 illustrates that the second actuation member 32 may be coupled to the body 16 of the first actuation member 13 via a pin 36, this is not intended to be limiting. Rather, it is contemplated that a variety of attachment technique may be utilized to couple the second actuation member 32 to the body 16 of the first actuation member 13. For example, it is contemplated that the second actuation member 32 may be welded, glued, etc. to the body 16 of the first actuation member 13.

Additionally, it can be appreciated that the engagement member 12a may be designed such that the first actuation member 13 and/or the second engagement member 32 bias the first jaw 18 and the second jaw 20 in a closed position (e.g., a position in which the first jaw 18 and the second jaw 20 contact one another). For example, the ends of the first jaw 18 and the second jaw 20 may contact one another while in a closed position. Positioning the first jaw 18 and the second jaw 20 together while in a closed position may permit a preload force to be generated when in the closed position.

FIG. 3 illustrates a side view of the first engagement member 12a. As described above, FIG. 3 illustrates a pair of jaws (e.g., the first jaw 18 facing the second jaw 20) extending away from the body portion 16 of the first actuation member 13. FIG. 3 further illustrates the curved portion 30 of each of the first jaw 18 and the second jaw 20 curving inward toward one another. Additionally, FIG. 3 illustrates the first attachment portion 24a extending away from the first end region 21 of the body 16. As discussed above, FIG. 3 illustrates that pin member 28 positioned within the first aperture 26a of the first attachment portion 24a. FIG. 3 further illustrates the second actuation member 32 coupled to the body 16 at the connection point 35 via the pin member 36. It can be appreciated from FIG. 3 that, in some examples, the second actuation member 32 may be positioned substantially perpendicular to the body 16 of the first actuation member 13.

In some instances it may be desirable to design the body 16 of the first actuation member 13 to include a specific aspect ratio. As described herein, the aspect ratio of the body 16 may be defined as the ratio of its length (approximately the distance from pin member 36 to the pin member 28) to its "width" (approximately the width of the body 16 which is substantially perpendicular to a longitudinal line extending between the pin member 36 and the pin member 28). In some examples, the aspect ratio of the body 16 should be at least 3:2 (e.g., the distance between the pin member 36 and the pin member 28 should be 1.5 times the "width" of the body 16, as discussed above). Further, in some examples, the aspect ratio should be larger than 3:2.

FIG. 4 illustrates another side view of the first engagement member 12a. It can be appreciated that the side view shown in FIG. 4 may be opposite to, and mirror, the side view illustrated in FIG. 3. Therefore, like FIG. 3, FIG. 4 illustrates the first jaw 18 facing the second jaw 20, whereby the first jaw 18 and the second jaw 20 extend away from the body portion 16 of the first actuation member 13. FIG. 4 further illustrates the curved portion 30 of each of the first jaw 18 and the second jaw 20 curving inward toward one another. Additionally, FIG. 4 illustrates the second attachment portion 24b extending away from the second end region 23 of the body 16. As discussed above, FIG. 4 illustrates that pin member 28 positioned within the second aperture 26b of the second attachment portion 24b. FIG. 4 further illustrates the second actuation member 32 coupled to the body 16 at the connection point 35 via the pin member 36. It can be appreciated from FIG. 4 that, in some examples, the second actuation member 32 may be positioned substantially perpendicular to the body 16 of the first actuation member 13.

Figure 5:
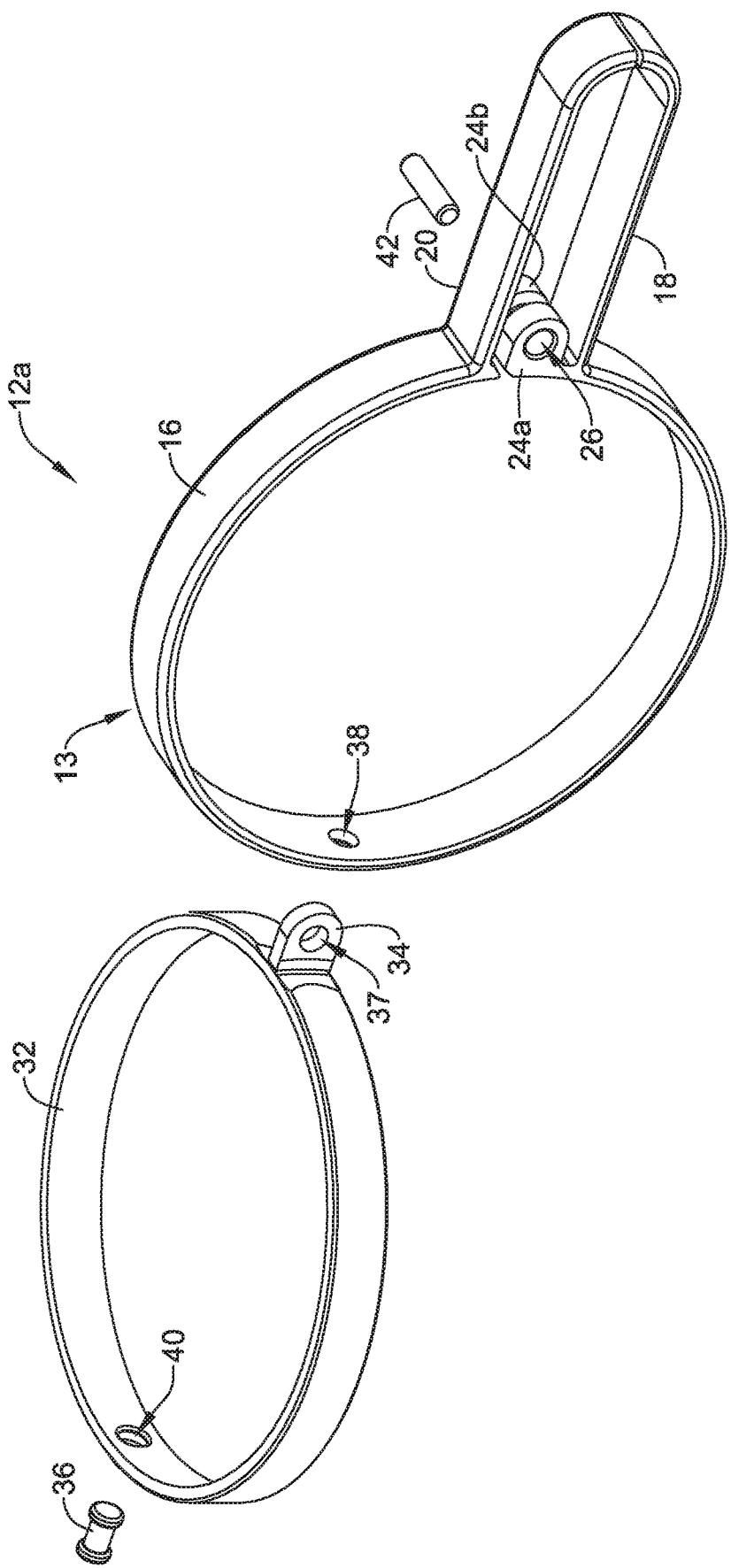
FIG. 5 is a perspective view of the example tissue engagement device shown in FIG. 1.

FIG. 5 illustrates an exploded view of the tissue engagement member 12a, including the first actuation member 13 and the second actuation member 32. As described above, the first actuation member 13 including the body portion 16, first jaw 18 and the second jaw 20. Further, FIG. 5 more clearly illustrates the first aperture 26a extending through the first attachment member 24a. Additionally, FIG. 5 illustrates a fourth aperture 38 through which the pin 36 (described above) may extend. It can further be appreciated from FIG. 5 that the body 16, the first jaw 18 and the second jaw 20 may lie within a single plane.

Additionally, FIG. 5 illustrates the second actuation member 32 including a projection 34 extending away therefrom. FIG. 5 further illustrates the third aperture 37 extending through the wall thickness of the projection 34. Further, FIG. 5 shows that that the second actuation member 32 may include a fifth aperture 40 through which the pin 36 may extend. As described above, the fourth aperture 38 of the body 16 may be aligned with the fifth aperture 40, thereby permitting the pin 36 to extend therethrough and couple the body 16 of the first actuation member 13 to the second actuation member 32.

It can further be appreciated from FIG. 5 that the second actuation member 32 may lie within a single plane which is offset from the plane in which the first actuation member 13 lies within. As discussed above, in some examples, the plane in which the first actuation member 13 lies may be substantially perpendicular to the plane in which the second actuation member lies. However, this is not intended to be limiting. Rather, it is contemplated that the plane in which the first actuation member 13 lies may be substantially offset to the plane in which the second actuation member lies.

As discussed above, FIG. 5 illustrates the pin member 42 which may be utilized to couple the first attachment portion 24a, the second attachment portion 24b and the projection 34 of the second actuation member 32. As will be discussed in greater detail below, the cylindrical design of the pin 42 may permit the first attachment portion 24a, the second attachment portion 24b and/or the second actuation member 32 to rotate therearound.

Figure 6:
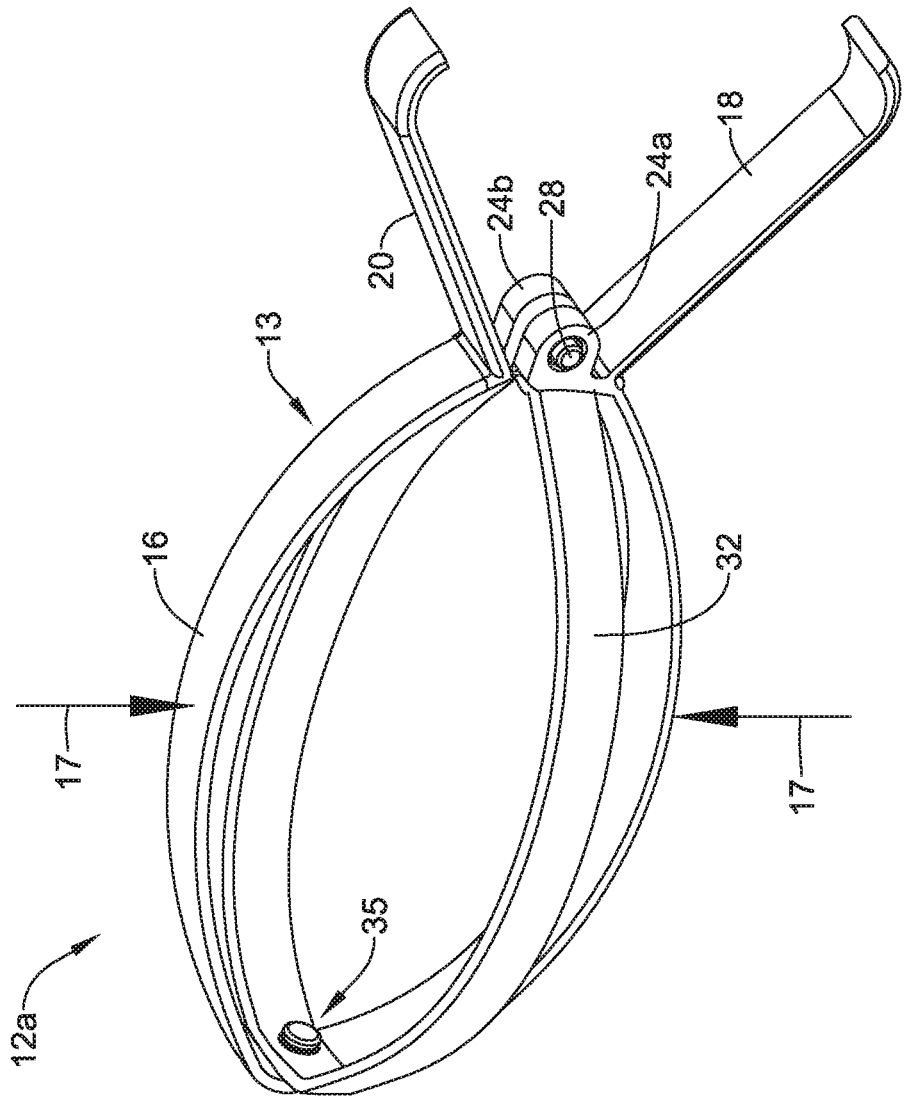
FIG. 6 is a perspective view of the example tissue engagement device shown in FIG. 1.
Figure 7:
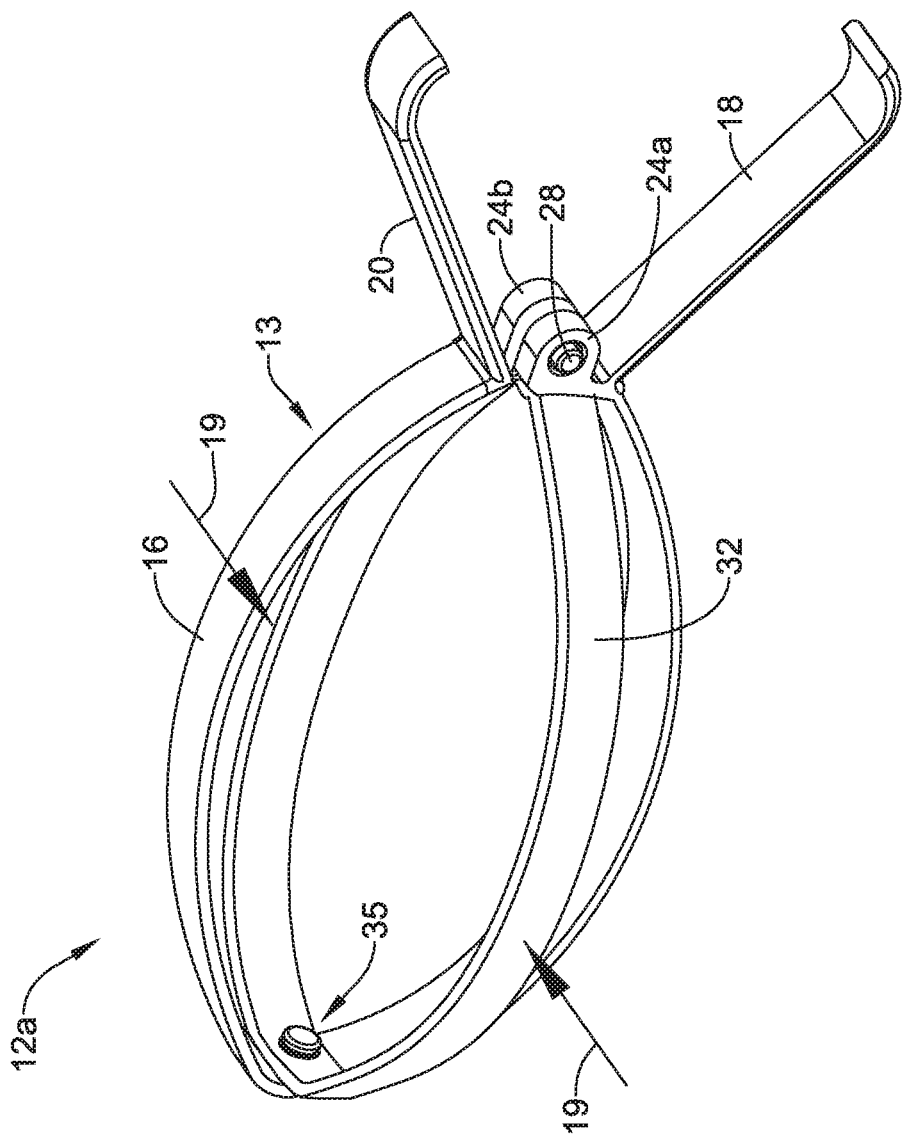
FIG. 7 is an exploded view of the example tissue engagement device shown in FIG. 1.

FIGS. 6 and 7 illustrate that the engagement member 12b may be designed such that actuation of the first actuation member 13, the second actuation member 32 or both the first actuation member 13 and the second actuation member 32 may shift the first jaw 18 and the second jaw 20 relative to one another. For example, the engagement member 12a may be designed such that a clinician may utilize a manipulator (not shown) to grasp and squeeze the first actuation member 13, the second actuation member 32 or both the first actuation member 13 which may shift the first jaw 18 relative to the second jaw 20.

For example, FIG. 6 shows the first jaw 18 and the second jaw 20 of the tissue retraction device 12a opened to an expanded configuration. Further, FIG. 6 illustrates that the first jaw 18 and the second jaw 20 may open to an expanded configuration when the body 16 of the first actuation member 13 is actuated (e.g. compressed, squeezed, etc.). The arrows 17 shown in FIG. 6 depict the actuation (e.g., compression) of the body 16 of the first actuation member 13. Further, it can be appreciated from FIG. 6 that as the body 16 is actuated (e.g., compressed) it may deform from a first configuration (e.g., the substantially circular configuration shown in FIG. 2) to a second configuration (e.g., the substantially ovular configuration shown in FIG. 6). As described above, other configurations are contemplated. It can further be appreciated that release of the compressive force applied to the body 16 of the first actuation member 16 may allow the first jaw 18 and the second jaw 20 to close and return to the configuration described above with respect to FIGS. 2-5.

FIG. 6 illustrates that as the body 16 of the first actuation member 13 is compressed, the body 16 may lengthen. It can be appreciated that the lengthening of the body 16 may cause the first attachment portion 24a and the second attachment portion 24b to rotate (e.g., pivot) around the pin member 28. It can be further appreciated that the rotation of the first attachment portion 24a and the second attachment portion 24b around the pin member 28 may result in the first jaw 18 shifting relative to the second jaw 20 (lengthening of the body 16 may result in the jaws shifting from a closed configuration to an open configuration).

Similar to FIG. 6, FIG. 7 shows the first jaw 18 and the second jaw 20 of the tissue retraction device 12a opened to an expanded configuration. Further, FIG. 7 illustrates that the first jaw 18 and the second jaw 20 may open to an expanded configuration when the second actuation member 32 is actuated (e.g. compressed, squeezed, etc.). The arrows 19 shown in FIG. 7 depict the actuation (e.g., compression) of the second actuation member 32. Further, it can be appreciated from FIG. 7 that as the actuation member 32 is actuated (e.g., compressed) it may deform from a first configuration (e.g., the substantially circular configuration shown in FIG. 2) to a second configuration (e.g., the substantially ovular configuration shown in FIG. 7). As described above, other configurations are contemplated. It can further be appreciated that release of the compressive force applied to the second actuation member 32 may allow the first jaw 18 and the second jaw 20 to close and return to the configuration described above with respect to FIGS. 2-5.

FIG. 7 illustrates that as the second actuation member 32 is compressed, it may lengthen. It can be appreciated that the lengthening of the second actuation member 32 may correspondingly lengthen the body 16 of the first actuation member 13 (as the second actuation member 32 is coupled to the first actuation member 13 at both the pivot point 22 and the connection point 35), and therefore, may cause the first attachment portion 24a and the second attachment portion 24b to rotate (e.g., pivot) around the pin member 28, as described above. It can be further appreciated that the rotation of the first attachment portion 24a and the second attachment portion 24b around the pin member 28 may result in the first jaw 18 shifting relative to the second jaw 20 (lengthening of the body 16 may result in the jaws shifting from a closed configuration to an open configuration).

Additionally, it can be appreciated from the above discussion that actuation of both the first actuation member 13 and the second actuation member 32 may lengthen the body 16, thereby causing the jaws to shift from a closed configuration to an open configuration. This feature is important as it may permit a clinician to grasp the engagement member 12a from a variety of different angles, all of which may permit the jaws to open. Further, the ability to grasp the engagement member 12a from a variety of different angles may reduce the time a clinician may spend having to shift the tissue retraction device 10 to a specific orientation in order to grasp it at a specific angle.

Figure 8:
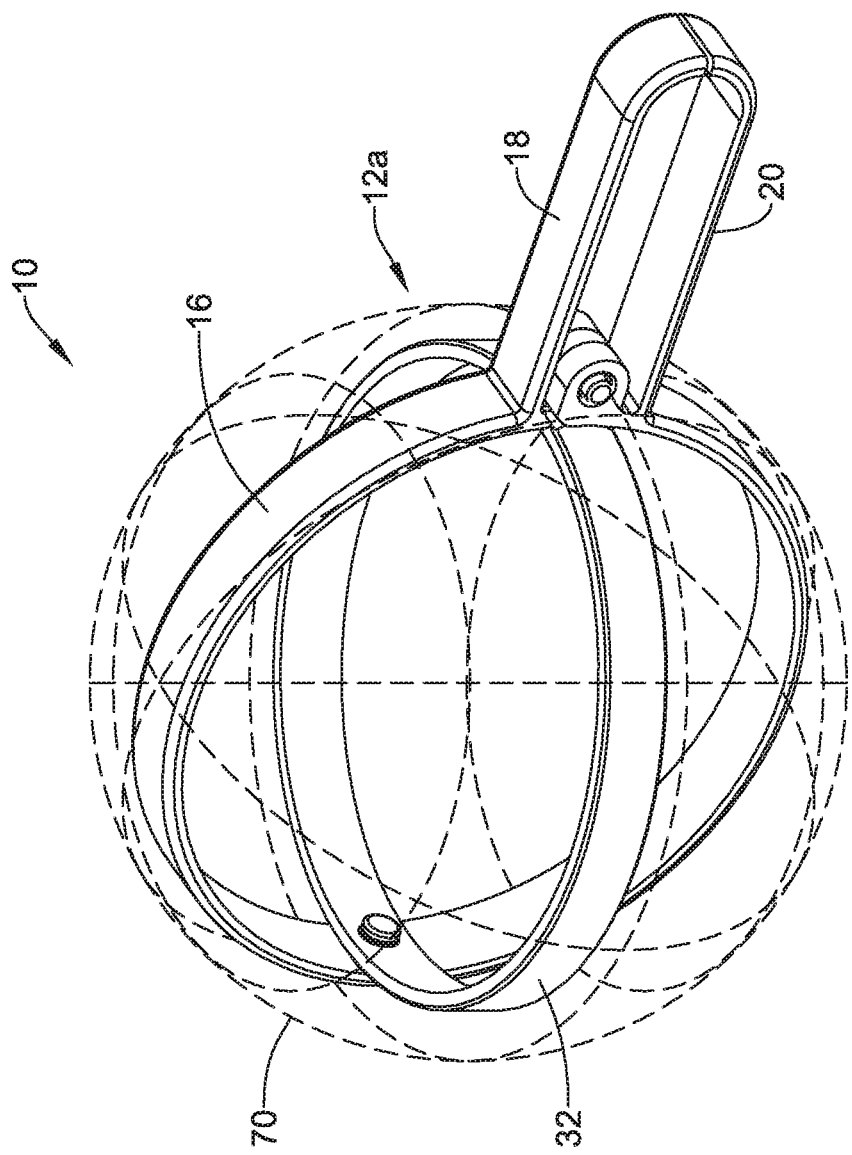
FIG. 8 is a perspective view of another example tissue engagement device.

To that end, FIG. 8 illustrates that in some examples, a portion of the engagement member 12a may include an actuation membrane (depicted by the dashed lines 70). As illustrated in FIG. 8, the membrane 70 may extend around a portion of the body 16 and/or the second actuation member 32. For example, the membrane 70 may extending around the body 16 and the second actuation member 32 while not covering the first jaw 18 and the second jaw 20. It can be appreciated that the membrane 70 may aid the actuation of the first actuation member 13, the second actuation member 32 or both. For example, the membrane 70 may be secured to the first actuation member 13, the second actuation member 32 or both the first actuation member 13 and the second actuation member 32 such that compressing/squeezing the membrane 70 may actuate the first actuation member 13, the second actuation member 32 or both the first actuation member 13 and open the jaw members.

FIG. 9 illustrates another example tissue engagement device 112. The tissue engagement device 112 may be similar in form and function to the tissue engagement device 12a described above. For example, the tissue engagement device 112 may include a first jaw 118 and a second jaw 120 coupled to one or more actuation members at a pivot location 122. In some instances (such as the example shown in FIG. 9), each of the first jaw 118 and the second jaw 120 may be directly attached to a first actuation member 132 and a second actuation member 133, respectively. Further, FIG. 9 illustrates that in some examples the first jaw 118 may be formed as a monolithic structure with the first actuation member 132. Similarly, FIG. 9 illustrates that in some examples the second jaw 120 may be formed as a monolithic structure with the second actuation member 133. FIG. 9 further illustrates that the each of the first actuation member 132 and the second actuation member 133 transitions to the first jaw 118 and the second jaw 120, respectively, at a first rotation point 150 and a second rotation point 152 formed within a framework 166.

Additionally, FIG. 9 illustrates that the engagement member 112 may include a third actuation member 116 and a fourth actuation member 117. As illustrated in FIG. 9, one end of each of the third actuation member 116 and the fourth actuation member 117 may be coupled to the framework 166 at a third rotation point 154 and a fourth rotation point 156, respectively. As will be described in greater detail below, the framework 166 may be designed to permit rotation of each end of the third actuation member 116 and the fourth actuation member 117 coupled to the framework 166. Additionally, FIG. 9 illustrates that an end of each of the first actuation member 132, the second actuation member 133, the third actuation member 116 and the fourth actuation member 117 may be coupled to another at a connection point 136. Similarly to that described above with respect to FIG. 2, a variety of designs, arrangements, structures, etc. may be utilized to couple the first actuation member 132, the second actuation member 133, the third actuation member 116 and the fourth actuation member 117 with one another at the connection point 136.

FIG. 10 illustrates a perspective view of the framework 166 including the first rotation point 150, the second rotation point 152, the third rotation point 154 and the fourth rotation point 156. Further, FIG. 10 illustrates that the first rotation point 150 may include the combined structure of the first actuation member 132 and the first jaw 118, whereby that combined structure is coupled to the framework 166 via a pin connection 158. Similarly, FIG. 10 illustrates that the second rotation point 152 may include the combined structure of the second actuation member 133 and the second jaw 120, whereby that combined structure is coupled to the framework 166 via a pin connection 160. Further, FIG. 10 illustrates that the third actuation member 116 may be coupled to the framework via a pin connection 162 and the fourth actuation member 117 may be coupled to the framework via a pin connection 164. It can be appreciated that each of these pin connections 158, 160, 162, 164 may permit a structure attached thereto to rotate. For example, pin connection 158 may permit rotation of an end region of both the first actuation member 132 and the first jaw 118. Similarly, the pin connection 160 may permit rotation of an end region of both the second actuation member 133 and the second jaw 120. Likewise, the pin connection 162 may permit rotation of the end region of the third actuation member 116 while the pin connection 164 may permit rotation of the end region of the fourth actuation member 117.

Similar to that described above, it can be appreciated that the combined actuation of any combination of the first actuation member 132, the second actuation member 133, the third actuation member 116 and/or the fourth actuation member 117 may lengthen (e.g., elongate) one or more of the first actuation member 132, the second actuation member 133, the third actuation member 116 and/or the fourth actuation member 117. In other words, actuation of any combination of the first actuation member 132, the second actuation member 133, the third actuation member 116 and/or the fourth actuation member 117 may lengthen the distance between the pivot point 122 and the connection point 136 (shown in FIG. 9). Further, this lengthening may cause rotation of the end regions of one or more of the first actuation member 132 and/or the second actuation member 133 at the first pin connection 158 and/or at the pin connection 160, respectively. It can be appreciated that rotation of the first actuation member 132 and/or the second actuation member 133 may cause rotation of the first jaw 118 and/or the second jaw 120. The rotation of the first jaw 118 and the second jaw 120 may correspond to a shifting of the jaws from closed configuration to an open configuration (and from an open configuration to a closed configuration as the actuation force is removed).

FIG. 11 illustrates another example tissue engagement device 212. The tissue engagement device 212 may be similar in form and function to the tissue engagement device 12a described above. For example, the tissue engagement device 212 may include a first jaw 218 and a second jaw 220 coupled to one or more actuation members at a pivot location 222. In some instances (such as the example shown in FIG. 11), each of the first jaw 118 and the second jaw 120 may be directly attached to a first actuation member 232 and a second actuation member 233, respectively. Further, FIG. 11 illustrates that in some examples the first jaw 218 may be formed as a monolithic structure with the first actuation member 232. Similarly, FIG. 11 illustrates that in some examples the second jaw 220 may be formed as a monolithic structure with the second actuation member 233. FIG. 11 further illustrates that the each of the first actuation member 232 and the second actuation member 233 transitions to the first jaw 218 and the second jaw 220, respectively, at a first rotation point 250 and a second rotation point 252 formed within a framework 266.

Additionally, FIG. 11 illustrates that the engagement member 212 may include a third actuation member 216 and a fourth actuation member 217. As illustrated in FIG. 11, one end region of each of the third actuation member 216 and the fourth actuation member 217 may be coupled to the framework 266 at a third rotation point 254 and a fourth rotation point 256, respectively. As will be described in greater detail below, the framework 266 may be designed to permit rotation of each end of the third actuation member 216 and the fourth actuation member 217 coupled to the framework 266. Additionally, FIG. 11 illustrates that an end of each of the first actuation member 232, the second actuation member 233, the third actuation member 216 and the fourth actuation member 217 may be coupled to another at a connection point 236. Similarly to that described above with respect to FIG. 2, a variety of designs, arrangements, structures, etc. may be utilized to couple the first actuation member 232, the second actuation member 233, the third actuation member 216 and the fourth actuation member 217 with one another at the connection point 136.

Further, FIG. 11 illustrates that the first rotation point 250 may include the combined structure of the first actuation member 232 and the first jaw 218, whereby that combined structure is coupled to the framework 266. Similarly, FIG. 11 illustrates that the second rotation point 252 may include the combined structure of the second actuation member 233 and the second jaw 220, whereby that combined structure is coupled to the framework 266.

Similar to that described above, it can be appreciated that the combined actuation of any combination of the first actuation member 232, the second actuation member 233, the third actuation member 216 and/or the fourth actuation member 217 may lengthen (e.g., elongate) one or more of the first actuation member 232, the second actuation member 233, the third actuation member 216 and/or the fourth actuation member 217. In other words, actuation of any combination of the first actuation member 232, the second actuation member 233, the third actuation member 216 and/or the fourth actuation member 217 may lengthen the distance between the pivot location 222 and the connection point 236. Further, this lengthening may cause rotation of the end regions of one or more of the first actuation member 232 and/or the second actuation member 233 at the first pin connection 258 and/or the second actuation member 260, respectively. It can be appreciated that rotation of the first actuation member 232 and/or the second actuation member 233 may cause rotation of the first jaw 218 and/or the second jaw 220. The rotation of the first jaw 218 and the second jaw 220 may correspond to a shifting of the jaws from closed configuration to an open configuration (and from an open configuration to a closed configuration as the actuation force is removed).

It should be noted that the features of any of the tissue retraction systems, tissue engagement members or components thereof described with respect to particular figures and/or embodiments are not limited to that particular example. Rather, it is contemplated that all of the features or examples disclosed with respect to a single example may be incorporated into any other example disclosed herein.

The materials that can be used for the various components of tissue retraction system 10 and the various devices disclosed herein may include those commonly associated with medical devices. For simplicity purposes, to the extent the following discussion makes reference to tissue retraction system 10, it is not intended to limit the devices and methods described herein only to tissue retraction system 10, as the discussion may be applied to other similar devices disclosed herein.

Tissue retraction system 10 and/or other components of tissue retraction system 10 may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether)phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro (propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP).

Some examples of suitable metals and metal alloys include stainless steel, such as 304V, 304L, 316LV, 17-4 and 400-series stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In at least some embodiments, portions or all of tissue retraction system 10 and/or other components of tissue retraction system 10 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of tissue retraction system 10 and/or other components of tissue retraction system 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of tissue retraction system 10 and/or other components of tissue retraction system 10 to achieve the same result.

In some embodiments, a degree of Magnetic Resonance Imaging (MRI) compatibility is imparted into tissue retraction system 10 and/or other components of tissue retraction system 10. For example, tissue retraction system 10 and/or other components of tissue retraction system 10, or portions thereof, may be made of a material that does not substantially distort the image and create substantial artifacts (e.g., gaps in the image). Certain ferromagnetic materials, for example, may not be suitable because they may create artifacts in an MRI image. Tissue retraction system 10 and/or other components of tissue retraction system 10, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. A tissue engagement device, comprising:
   a first actuation member including a body extending between a pivot point and a fixation point and coupled to a first jaw and a second jaw at the pivot point, wherein the body is designed to shift between a first configuration and a first compressed configuration; and
   a second actuation member coupled to the first actuation member at the pivot point and at the fixation point, wherein the second actuation member is designed to shift between a second configuration and a second compressed configuration;
   wherein shifting the first actuation member from the first configuration to the first compressed configuration and shifting the second actuation member from the second configuration to the second compressed configuration, shifts the first jaw and the second jaw between a closed configuration and an open configuration.

2. The tissue engagement device of claim 1, wherein the second actuation member is positioned substantially perpendicular to the first actuation member.

3. The tissue engagement device of claim 1, wherein the body, the first jaw and the second jaw are formed from a monolithic member.

4. The tissue engagement device of claim 1, wherein the body, the second actuation member or both the body and the second actuation member include an arcuate portion.

5. The tissue engagement device of claim 1, wherein the body, the second actuation member or both the body and the second actuation member are substantially circular or ovular.

6. The tissue engagement device of claim 1, wherein shifting the first actuation member, the second actuation member or both the first and second actuation members rotates the first jaw and the second jaw around the pivot point.

7. The tissue engagement device of claim 1, further comprising a compression membrane positioned around at least a portion of the body, the second actuation member or both the body and the second actuation member.

8. The tissue engagement device of claim 1, wherein the first jaw and the second jaw are biased in the closed configuration.

9. The tissue engagement device of claim 1, wherein the first configuration of the first actuation member and the second configuration of the second actuation member extend from the pivot point to the fixation point.

10. The tissue engagement device of claim 1, wherein when at least one of the first actuation member is shifted into the first compressed configuration or the second actuation member is shifted into the second compressed configuration, the distance between the pivot point and the fixation point increases.

11. A tissue engagement device, comprising:
   a first actuation member including a first end having a first jaw, a second end having a second jaw, and a looped region positioned between the first jaw and the second jaw, wherein the first jaw, the second jaw and the looped region lie within a first plane; and
   a second actuation member pinned to the first actuation member at a pivot point and a fixation point, wherein the second actuation member lies in a second plane transverse to the first plane;
   wherein actuation of the first actuation member along the first plane, or actuation of the second actuation member along the second plane, or actuation of both the first and second actuation members along the first and second planes, respectively, shifts the first jaw and the second jaw between a closed configuration and an open configuration.

12. The tissue engagement device of claim 11, wherein the second plane is positioned substantially perpendicular to the first plane.

13. The tissue engagement device of claim 11, wherein the first actuation member, the first jaw and the second jaw are formed from a monolithic member.

14. The tissue engagement device of claim 11, wherein the first actuation member, the second actuation member or both the first and the second actuation members include an arcuate portion.

15. The tissue engagement device of claim 11, wherein the first actuation member, the second actuation member or both the first and the second actuation members are substantially circular or ovular.

16. The tissue engagement device of claim 11, wherein actuation of the first actuation member, the second actuation member or both the first and second actuation members rotates the first jaw and the second jaw around the pivot point.

17. The tissue engagement device of claim 11, further comprising a compression membrane positioned around at least a portion of the first actuation member, the second actuation member or both the first and the second actuation member.

18. The tissue engagement device of claim 11, wherein the first jaw and the second jaw are biased in the closed configuration.

* * * * *